United States Patent [19]
Rabenau et al.

[11] Patent Number: 5,972,028
[45] Date of Patent: Oct. 26, 1999

[54] STENT HOLDER/COMPRESSION INSTRUMENT

[75] Inventors: Richard Rabenau, Birmingham; Rowland W. Kanner, Guntersville; Fred E. Williams, Jr., Arab, all of Ala.

[73] Assignee: Atrion Medical Products, Inc., Arab, Ala.

[21] Appl. No.: 09/006,748

[22] Filed: Jan. 13, 1998

Related U.S. Application Data

[60] Provisional application No. 60/061,302, Oct. 7, 1997.

[51] Int. Cl.⁶ ..................................................... A61F 2/06
[52] U.S. Cl. ................................................................ 623/1
[58] Field of Search ................................... 623/1, 11, 12; 606/1, 8, 194, 195, 198; 604/104

[56] References Cited

U.S. PATENT DOCUMENTS

| | | |
|---|---|---|
| 5,168,757 | 12/1992 | Rabenau et al. . |
| 5,378,237 | 1/1995 | Boussignac et al. . |
| 5,484,449 | 1/1996 | Amundson et al. . |
| 5,626,604 | 5/1997 | Cottone ........................................ 606/1 |
| 5,628,754 | 5/1997 | Shevlin .................................... 606/195 |
| 5,662,703 | 9/1997 | Yurek ....................................... 606/195 |
| 5,672,169 | 9/1997 | Verbeek ...................................... 623/1 |
| 5,725,519 | 3/1998 | Penner ......................................... 606/1 |
| 5,738,674 | 4/1998 | Williams .................................. 606/108 |
| 5,746,764 | 5/1998 | Green ...................................... 606/194 |
| 5,785,715 | 7/1998 | Schatz ..................................... 606/108 |
| 5,868,753 | 2/1999 | Schatz ..................................... 606/195 |

*Primary Examiner*—Michael J. Milano
*Attorney, Agent, or Firm*—Trexler, Bushnell, Giangiorgi & Blackstone, Ltd.

[57] ABSTRACT

A novel stent compression instrument is used for holding a stent therein during shipping to a hospital and for thereafter crimping the stent onto a balloon catheter. The stent compression instrument includes a body having a central bore; a flexible diaphragm having an axial lumen and mounted within the body central bore, thereby defining a chamber between the body and the diaphragm, and first and second sealing structures for providing seals at opposite ends of the chamber. The diaphragm is formed from a generally tubular, thin wall into which the stent is placed therein and is expandable under a negative pressure condition to expand within the body and compressible under pressure to crimp the stent onto a balloon catheter. Holding structure, which is formed from at least one thickened wall portion along the length of the diaphragm wall, is associated with the diaphragm for holding the stent therewithin and to prevent movement of the stent once positioned therewithin when the diaphragm is subjected to a negative pressure condition. In the preferred embodiment, positioning structure is provided which is formed from a thickened wall portion along the length of the diaphragm wall which is spaced from the holding structure, is also associated with the diaphragm for positioning the stent within the lumen and preventing the further axial movement of the stent relative to the lumen when the stent is placed therein.

58 Claims, 10 Drawing Sheets

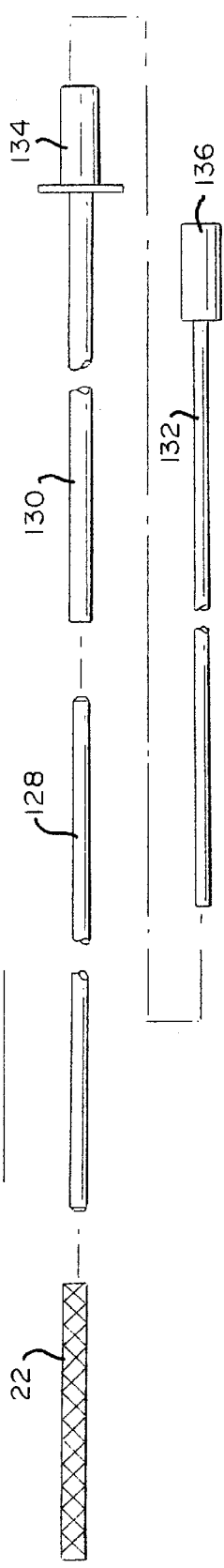
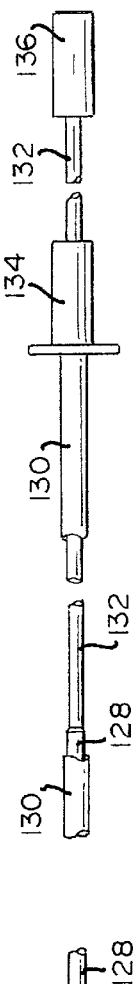
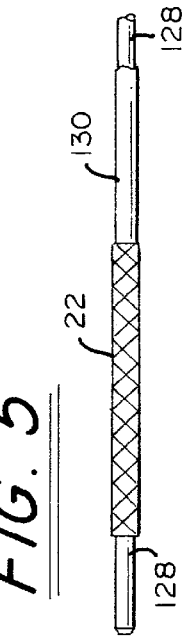
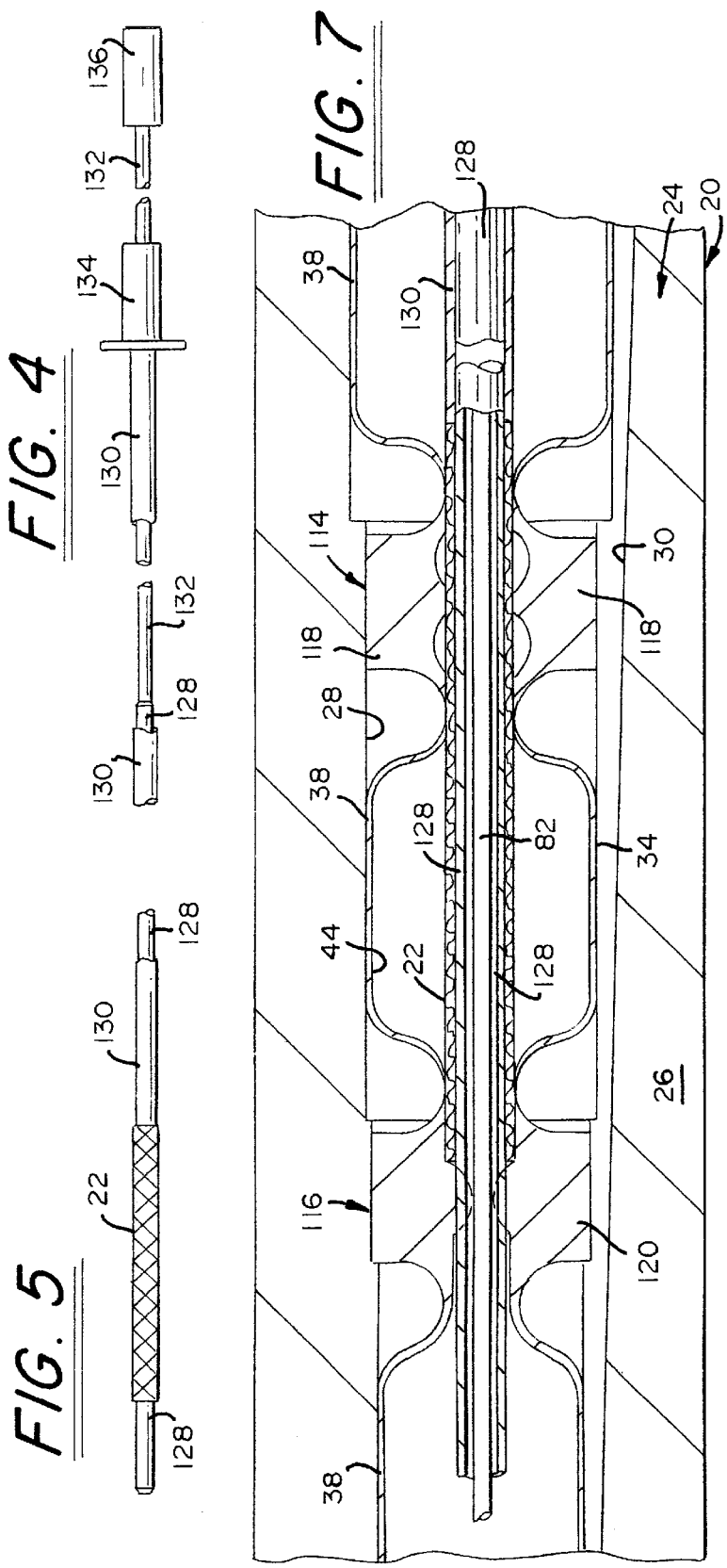

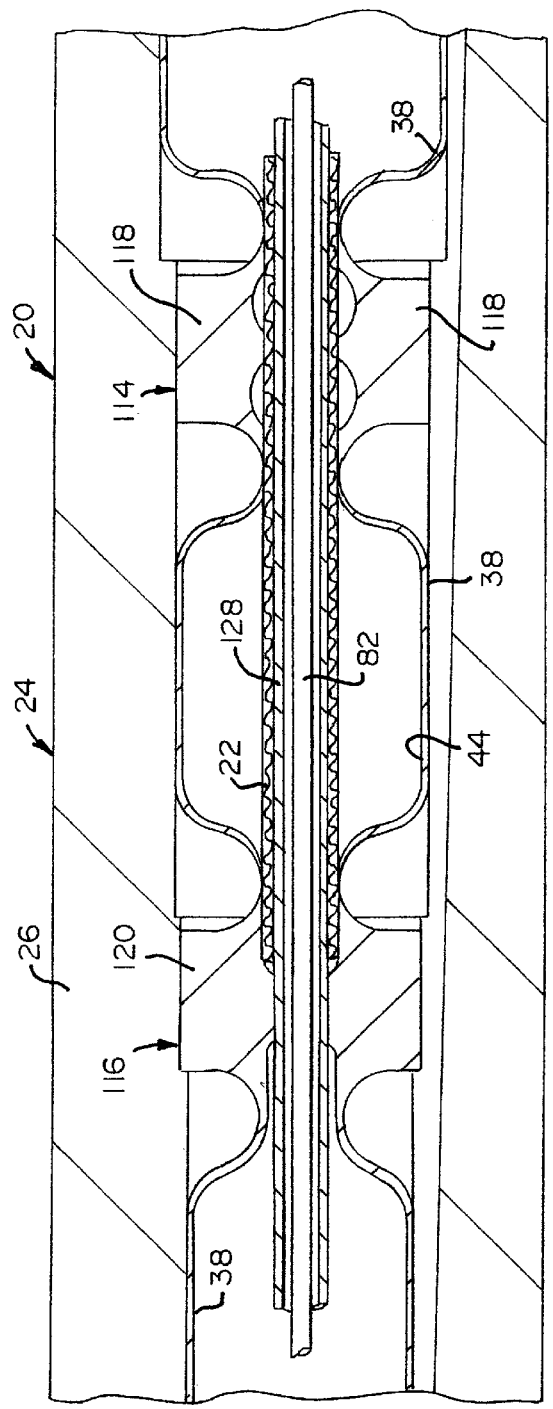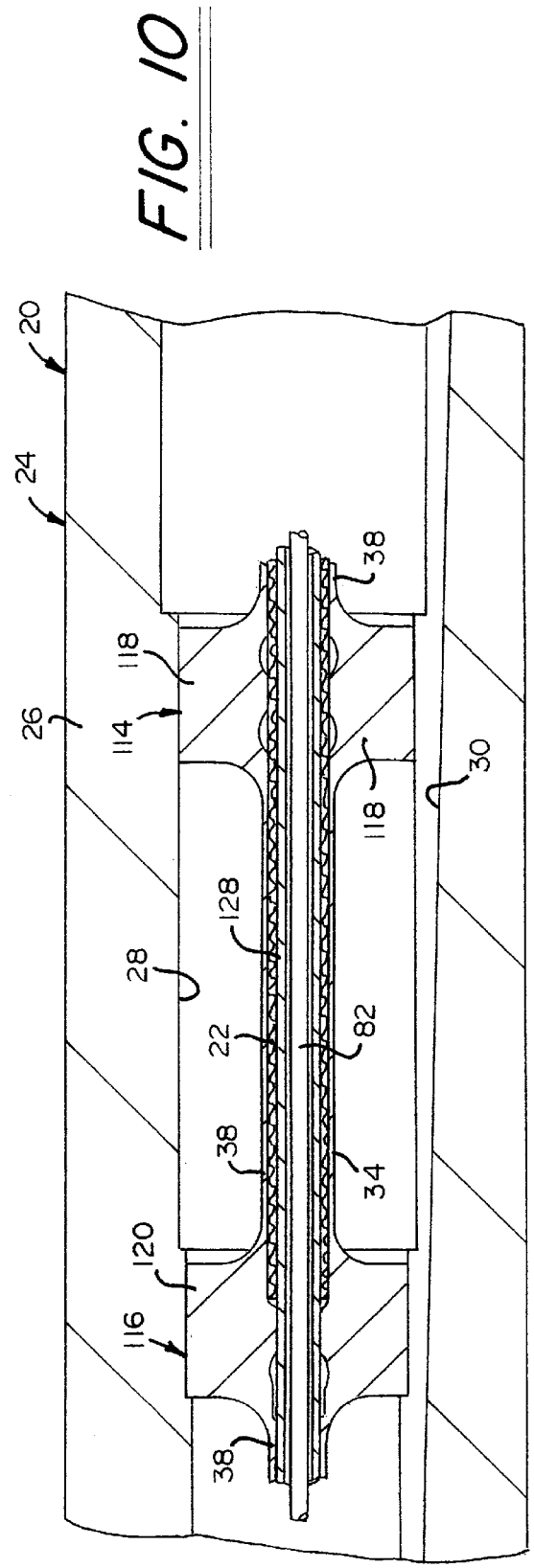

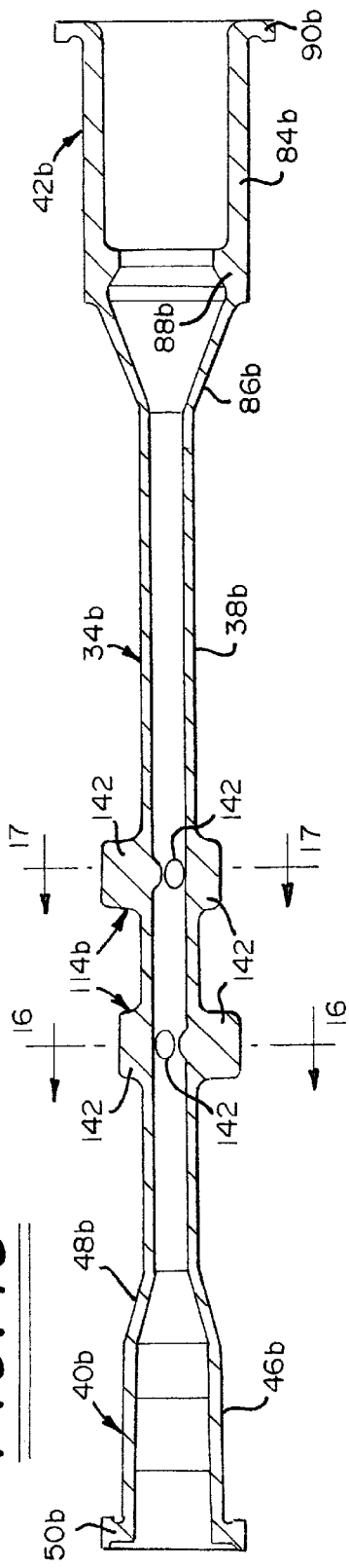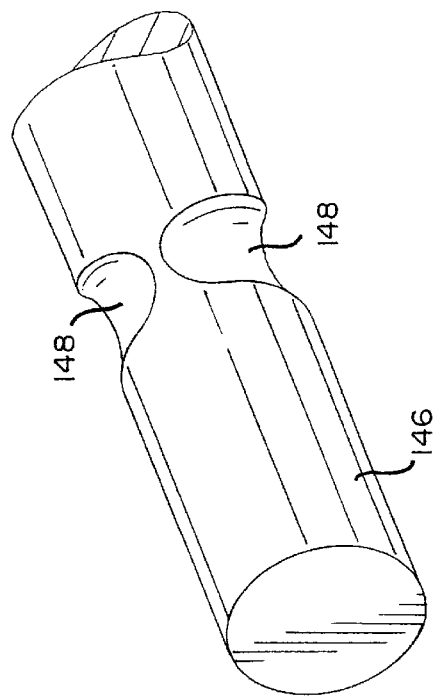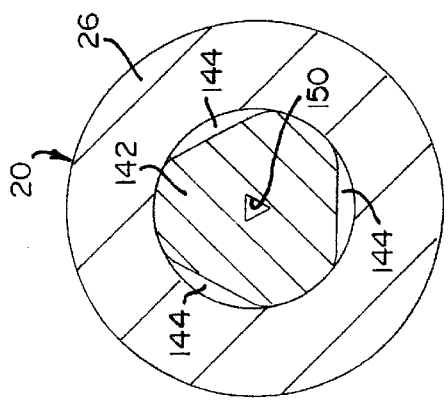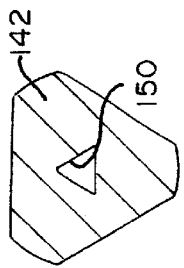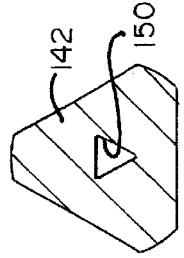

STENT HOLDER/COMPRESSION INSTRUMENT

This application is based on Provisional Application Ser. No. 60/061,302, filed on Oct. 7, 1997, entitled "Stent Holder/Compression Instrument".

BACKGROUND OF THE INVENTION

This invention is directed to a novel stent holder/compression instrument for holding and properly positioning a stent therein, in which the stent can be positioned and held without handling by an operator. The present invention is further directed to a novel method for positioning a stent within the novel stent holder/compression instrument. This invention is further directed to a novel instrument which can be used to ship a stent to a hospital and thereafter be used to crimp the stent onto a balloon catheter.

In order to improve the effectiveness of vascular angioplasty in relieving blockage or repairing cardiovascular damage, an expandable stainless steel mesh stent of tubular configuration has been developed for vascular implantation. The mesh stent is used to prevent arteries from closing (restenosis) after vascular balloon angioplasty. The stent is introduced into the artery by a balloon catheter on which the stent has been previously crimped and the stent is then dilated against the vascular implantation site by expansion of the balloon catheter. Precisely locating, implanting and expanding the stent requires that it be securely carried on the balloon catheter for both transport to the implantation site and expansion by the balloon.

A stent compression instrument is disclosed in U.S. patent application Ser. No. 08/745,317 which is commonly owned by the assignee herein, and employs a thin, elastomeric tubular diaphragm inside a housing to exert uniform forces on a stent to compress the stent onto and around a balloon catheter. The disclosure of said prior application is incorporated herein by reference. A stent in a neutral expanded state is placed over a balloon section of a catheter. The tubular diaphragm within the housing is expanded and the stent and balloon catheter are placed inside the diaphragm of the compression instrument. As pressurization forces are applied to the diaphragm, the stent is compressed and collapsed until the stent is rigidly and uniformly affixed to the balloon catheter. The stent loaded catheter is now ready for use and subsequent expansion of the stent by the catheter during implantation. This method requires handling of both the stent and the balloon catheter during the attachment or crimping procedure.

Improved stents with a delicate coating which enhances and improves the stent's efficacy are currently being tested and considered for use. The coatings could be damaged, by touching for example, during this handling phase.

The present invention provides a novel stent holder/compression instrument and method for attaching an expandable stent to a balloon catheter which eliminates the handling of the stent by an operator during attachment. The present invention also provides a novel instrument which can be used to ship a stent to a hospital and thereafter be used to crimp the stent onto a balloon catheter. Other features and advantages of the present invention will become apparent upon a reading of the attached specification in combination with an examination of the drawings.

SUMMARY OF THE INVENTION

A general object of the present invention is to provide a novel stent holder/compression instrument which is used to hold and properly position an expandable metal mesh stent therein such that the stent holder/compression instrument can be pre-loaded at the factory with a stent.

Another general object of the present invention is to provide a novel method of loading a stent into a stent holder/compression instrument without direct handling of the stent by an operator.

Yet another general object of the present invention is to provide a novel instrument which can be used to ship a stent to a hospital and thereafter be used to crimp the stent onto a balloon catheter.

An object of the present invention is to provide a novel stent holder/compression instrument which has a diaphragm that is designed to prevent blow-outs which tend to occur with thin-walled prior art diaphragms.

A further object of the present invention to provide a novel stent holder/compression instrument which includes a guide wire that allows for easier catheter loading, maintains proper catheter placement, and reduces the potential for blow-outs of the diaphragm.

Briefly, and in accordance with the foregoing, the present invention discloses a novel stent holder/compression instrument and method of use thereof, for holding a stent therein during shipping to a hospital and for crimping the stent onto a balloon catheter. The stent holder/compression instrument includes a body having a central bore; a flexible diaphragm having an axial lumen and mounted within the body central bore, thereby defining a chamber between the body and the diaphragm, and first and second sealing structures for providing seals at opposite ends of the chamber. The diaphragm is formed from a generally tubular, thin wall into which the stent is placed therein. The tubular, thin wall is expandable under a negative pressure condition to expand within the body and compressible under pressure to crimp the stent onto a balloon catheter. A holding structure, which is formed from at least one thickened wall portion along the length of the diaphragm wall, is associated with the diaphragm for holding the stent therewithin and to prevent movement of the stent once positioned therewithin when the diaphragm is subjected to a negative pressure condition. In the preferred embodiment, a positioning structure, which is formed from a thickened wall portion along the length of the diaphragm wall which is spaced from the holding structure, is also associated with the diaphragm for positioning the stent within the lumen and preventing the further axial movement of the stent relative to the lumen when the stent is placed therein.

To insert the stent into the novel stent holder/compression instrument, a negative pressure condition is formed around the diaphragm such that the diaphragm is expanded. Next, a tubular mandrel is inserted into an end of a tubular push sleeve and an eject rod is inserted into the opposite end of the tubular push sleeve until the mandrel and the eject rod contact each other. Thereafter, the stent is mounted on the mandrel without handling the stent, and the mandrel, having the stent mounted thereon, is inserted into the diaphragm lumen until the stent contacts the positioning structure in the preferred embodiment or the holding structure in the alternate embodiment. The stent is also lightly gripped by the holding structure. The push sleeve and the eject rod are then removed, leaving the mandrel and the stent within the diaphragm lumen. In the preferred embodiment, if initial insertion of the mandrel and stent does not cause the stent to engage against the positioning structure, the push sleeve is used to push the stent thereagainst prior to removal of the push sleeve and the eject rod from within the stent holder/ compression instrument. Thus, the stent is positioned within the diaphragm without direct handling by an operator. The stent holder/compression instrument can now be shipped with the stent factory pre-loaded.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 3 is a side elevational view of a mesh stent in a neutral condition and a side elevational view of an assembly that is used to insert the stent within the stent holder/compression instrument shown in FIG. 1, with the elements that form the assembly shown fragmentarily;

FIG. 4 is a partial, side elevational view of a portion of the assembly of FIG. 3, shown fragmentarily, and showing a step in the assembly thereof;

FIG. 5 is a partial, side elevational view of a portion of the assembly of FIG. 3, shown fragmentarily, and showing the final step in the assembly thereof;

FIG. 7 is an enlarged, cross-sectional view of the stent holder/compression instrument shown in FIG. 1, with the diaphragm therein being subjected to a negative pressure condition and with the assembly of FIG. 5 inserted therein and shown partially in cross-section;

FIG. 9 is an enlarged cross-sectional view of a portion of the stent holder/compression instrument shown in FIG. 1 having the stent positioned within the diaphragm which is being subjected to a negative pressure condition;

FIG. 10 is an enlarged cross-sectional view of the portion of the stent holder/compression instrument shown in FIG. 9 having the stent positioned within the diaphragm which is not being subjected to a negative pressure condition;

FIG. 15 is a cross-sectional view of a third embodiment of the diaphragm;

FIG. 16 is a cross-sectional view along line 16—16 of FIG. 15;

FIGURE 17 is a cross-sectional view along line 16—16 of FIG. 15;

FIG. 18 is a cross-sectional view of the diaphragm inserted into the stent holder/compression instrument; and FIG. 19 is a portion of a tool used to form the diaphragm of FIG. 15.

DETAILED DESCRIPTION OF THE PREFERRED EMBODIMENT

Figure 1:
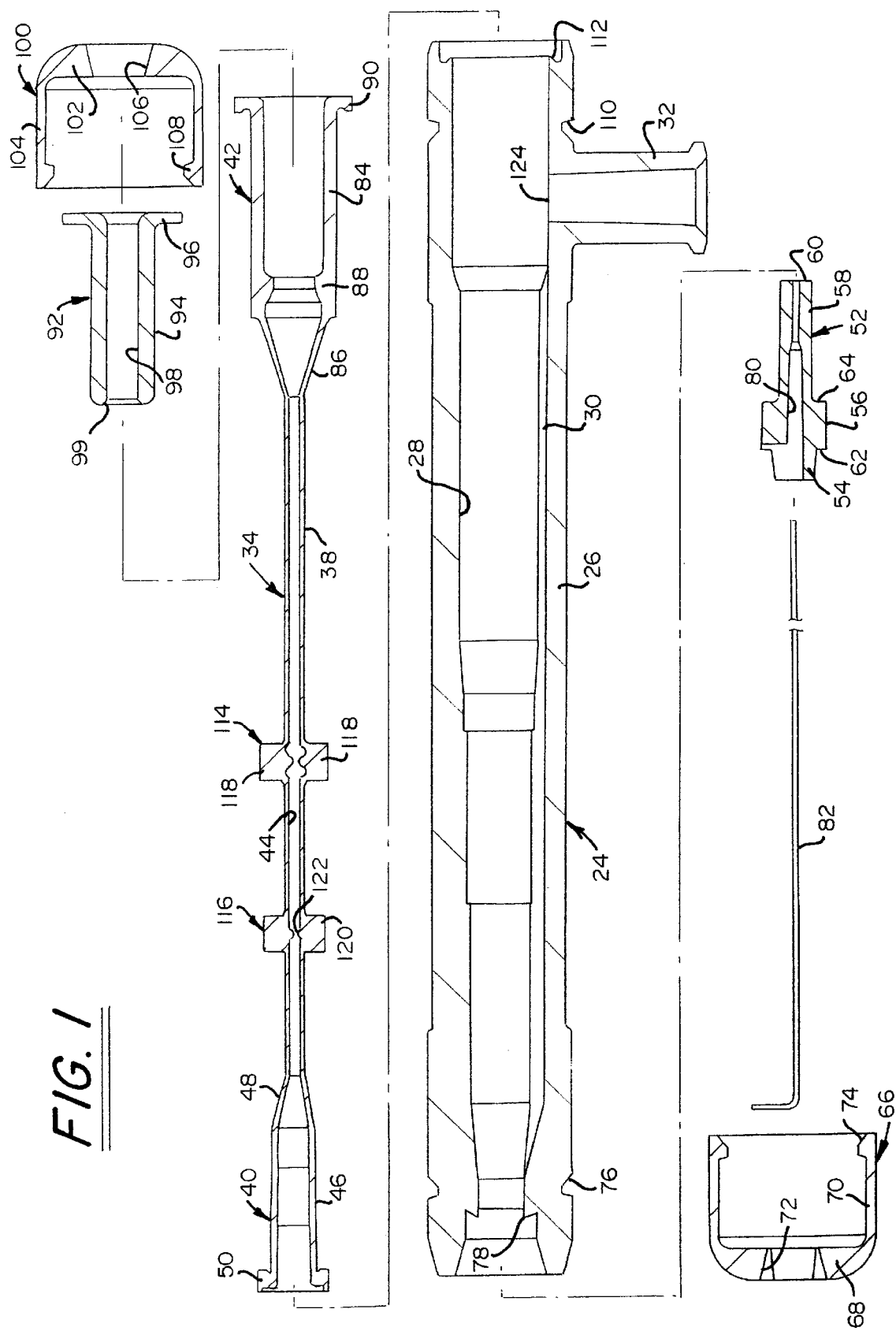
FIG. 1 is an exploded, cross-sectional view of a novel stent holder/compression instrument which incorporates the features of the invention.

While the invention may be susceptible to embodiment in different forms, there is shown in the drawings, and herein will be described in detail, specific preferred embodiments with the understanding that the present disclosure is to be considered an exemplification of the principles of the invention, and is not intended to limit the invention to the embodiment or embodiments as illustrated and described herein.

Figure 12:
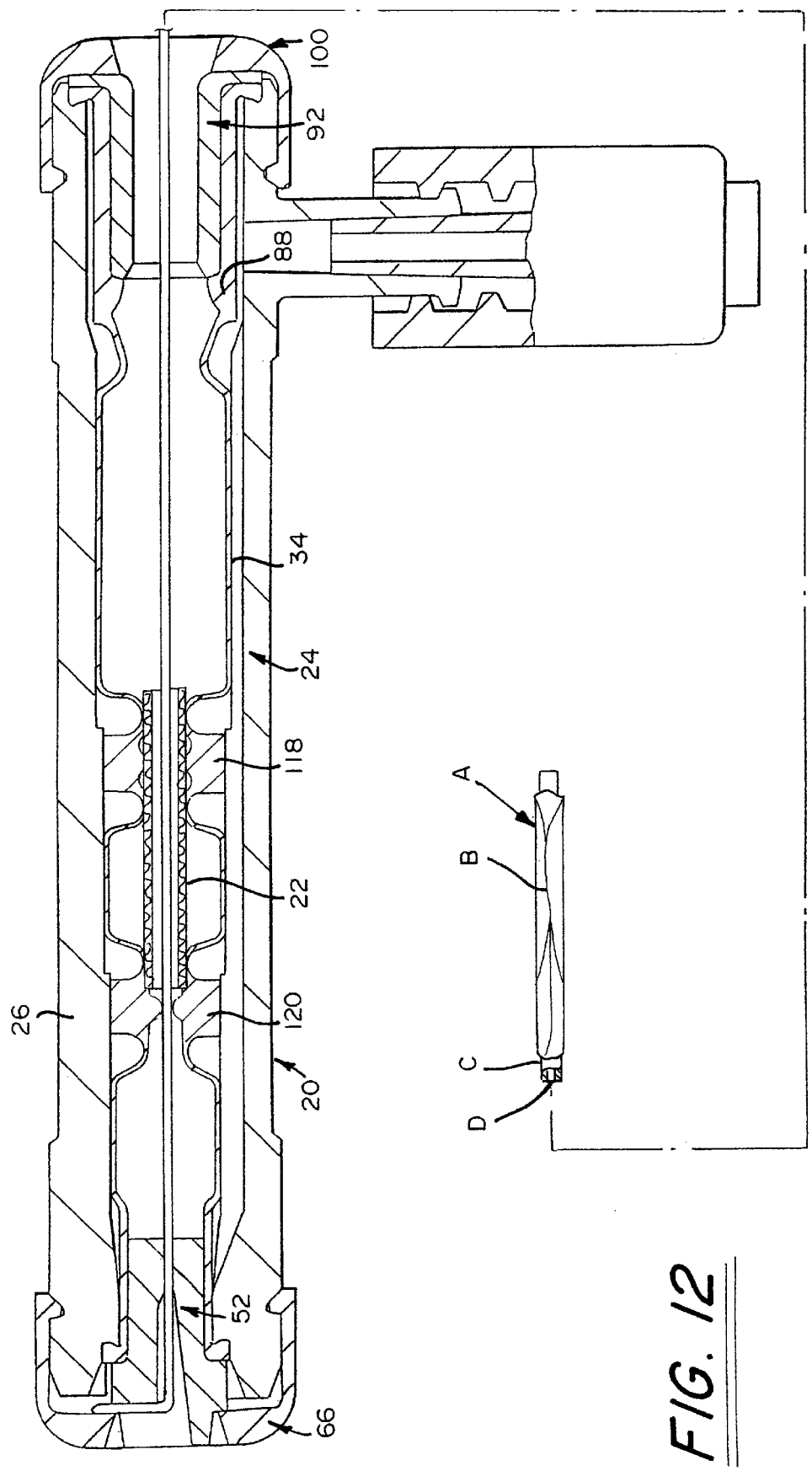
FIG. 12 is a cross-sectional view of the stent holder/compression instrument shown in FIG. 1, with the diaphragm therein being subjected to a negative pressure condition and having the stent positioned therein with a balloon catheter shown in side elevation, partially broken away and exploded from the stent holder/compression instrument.

The present invention presents a novel stent holder/compression instrument 20 which is used as a protective shipping device for a stent 22 as well as an instrument for mounting the stent 22 onto a balloon catheter A and a novel method associated with handling, using and packaging of a stent 22, particularly improved stents. An improved stent 22 of this type may have received delicate surface coating which enhances the stent's efficacy. In addition to the holding function provided by the stent holder/compression instrument 20 of the present invention, the stent holder/compression instrument 20 is also used to uniformly crimp or compress the stent 22 onto a conventional balloon catheter A (see FIG. 12 for a drawing of the balloon catheter A), as described herein.

The stent holder/compression instrument 20 includes a body 24 formed from a generally tubular wall 26 having an inner wall which defines a central through bore 28. An internal, elongate groove 30 is formed along the length of the body inner wall. A fluid coupling 32 is integrally formed with the tubular wall 26 and is a generally tubular member which communicates with the elongate groove 30 in the tubular wall 26 as described herein. The body 24 is preferably plastic and is molded to withstand internal pressures of 450 psi or greater during the stent compression operation.

Figure 13:
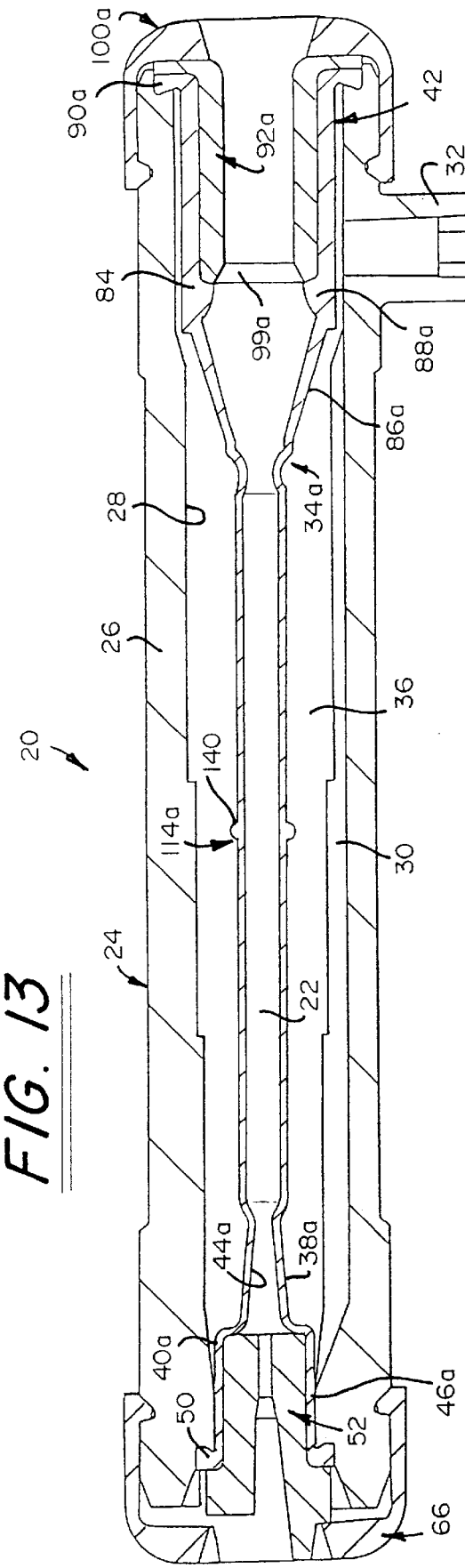
FIG. 13 is a cross-sectional view of the stent holder/compression instrument, with a second embodiment of the diaphragm positioned therein and which is in a neutral position having the stent positioned therein.

An elongated, flexible, generally tubular diaphragm is mounted within the central bore 28 of the body 24. A first embodiment of the diaphragm 34 is shown in FIGS. 1, 2 and 6–12, a second embodiment of the diaphragm 34a is shown in FIG. 13 and a third embodiment of the diaphragm 34b is shown in FIGS. 15–18. Like elements in each embodiment are denoted with like reference numerals with the elements of the second embodiment having an "a" after the numeral and the elements of the third embodiment having a "b" after the numeral.

Attention is now directed to the first embodiment of the diaphragm 34 which is shown in FIGS. 1, 2 and 6–12. The ends of the diaphragm 34 are sealed to the body 24 as described herein to form a pressure chamber 36 between the diaphragm 34 and the body 24, see FIG. 2. The diaphragm 34 has an elongated, thin wall section 38 along a central portion thereof which is generally tubular and which is integrally formed with first and second end sections 40, 42, respectively. A central through lumen 44 extends axially along the length of the diaphragm 34. The diaphragm 34 is formed from an elastomer, preferably silicone and preferably G.E. L.I.M. silicone rubber, durometer 25-55 shore A, capable of withstanding a 450 psi or greater pressure externally applied for transmission to the stent 22 inserted within the diaphragm 34 during the stent compression operation as described herein.

The first end section 40 of the diaphragm 34 is formed from an elongated, generally annular wall 46 which has an inner diameter that is greater than the inner diameter of the central wall section 38. The wall which forms the generally annular wall 46 is thickened relative to the wall that forms the central wall section 38 for reasons described herein. A connecting wall 48 tapers gradually from the enlarged, generally annular wall 46 to the central thin wall section 38. An annular sealing ring 50 is provided at the opposite end of the wall 46 and extends generally perpendicular to the wall 46. The inner diameter of the portion of the diaphragm lumen 44 in the wall 46 is greater than the inner diameter of the lumen 44 in the central wall section 38 and the inner diameter of the lumen 44 gradually tapers in the connecting wall 48 from the enlarged inner diameter in the wall 46 to the smaller inner diameter in the central wall section 38.

Figure 2:
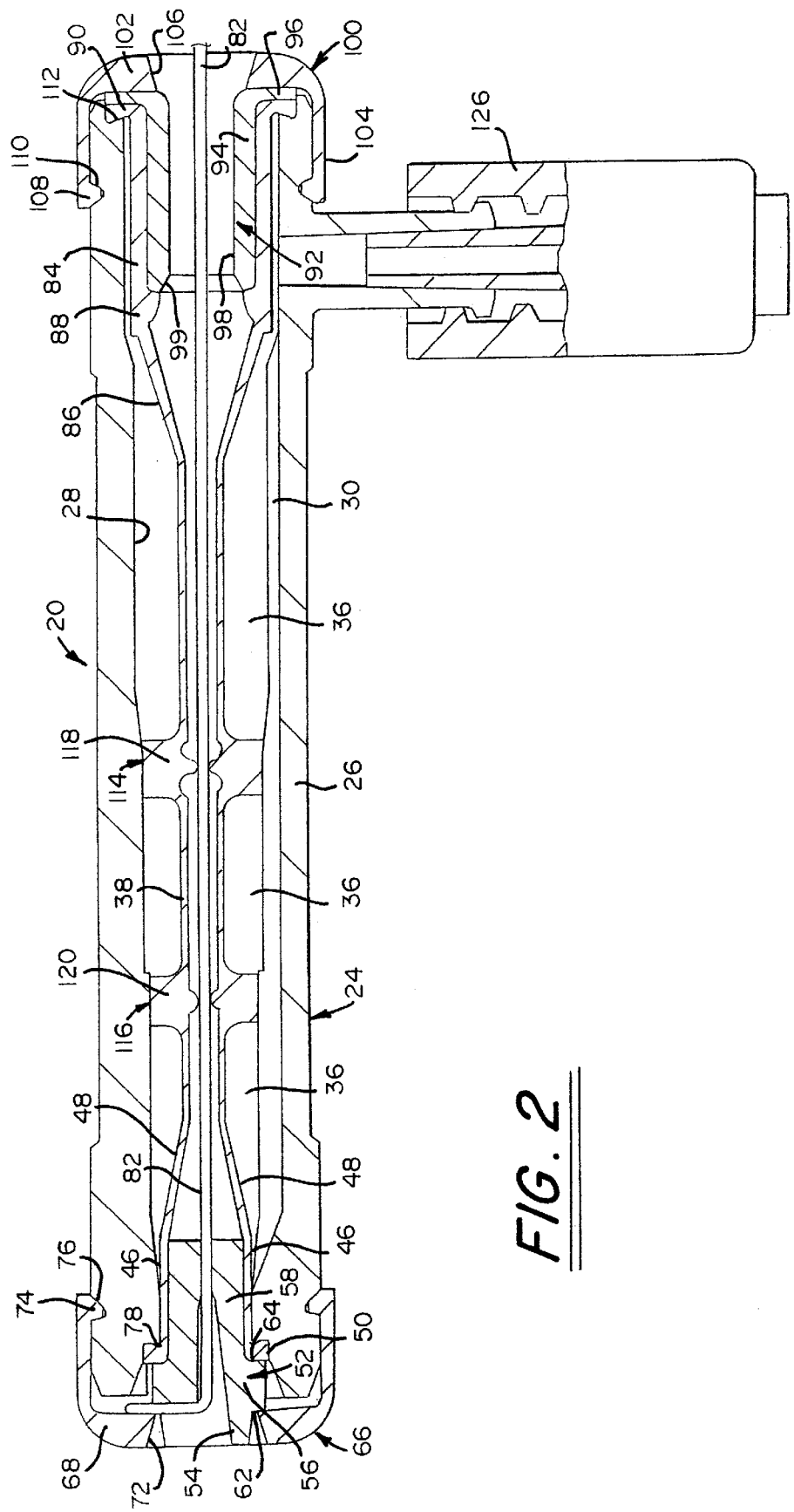
FIG. 2 is an assembled, cross-sectional view of the stent holder/compression instrument shown in FIGURE 1.

As shown in FIG. 2, a plastic ferrule 52 is inserted into the portion of the diaphragm lumen 44 in the wall 46 to clamp the sealing ring 50 and a portion of the wall 46 against the body wall 26 to seal one end of the pressure chamber 36 between the diaphragm 34 and the body wall 26. The ferrule 52 is formed from a first generally conical portion 54 having opposite ends, a second cylindrical portion 56 having opposite ends and which is integrally formed with one of the ends of the first portion 54 and has an outer diameter that is greater than the outer diameter of the first portion 54, and a third cylindrical portion 58 having opposite ends and which is integrally formed with the opposite end of the second portion 56 and has an outer diameter that is approximately equal to the outer diameter of the first portion 54. The opposite end of the third portion 58 defines an end surface 60 upon which the balloon catheter A abuts as described herein. The increase in outer diameter between the first portion 54 and the second portion 56 forms a shoulder 62 on the second portion 56 for mating with a plastic end cap 66 as described herein. The increase in outer diameter between the second portion 56 and the third portion 58 forms a shoulder 64 on the second portion 56 for mating against the sealing ring 50 of the diaphragm 34 to sandwich the sealing ring 50 between the shoulder 64 and the body wall 26.

The end cap 66 snap-fits with the body wall 26 to maintain the ferrule 52 in position and to maintain the clamp between the shoulder 64, the sealing ring 50 and the body wall 26. The end cap 66 includes an end wall 68 and an annular skirt 70 which depends therefrom. The annular end wall 68 has a through bore 72 therethrough into which the first portion 54 of the ferrule 52 is inserted as shown in FIG. 2. An internal, annular protrusion 74 projects inwardly from the annular skirt 70 and mates with an annular groove 76 that is provided in the external surface of the body wall 26 at a distance that is spaced from the end of the body wall 26 to provide a snap-fit of the end cap 66 with the body 24. The annular end wall 68 of the end cap 66 abuts against the ferrule shoulder 62 when the end cap 66 is snap-fit to the body wall 26 to maintain the ferrule 66 within the diaphragm lumen 44 and to maintain the seal between the ferrule 66, the sealing ring 50 and the body 24. The body wall 26 has a raised seal ring 78 at the point at which the sealing ring 50 is compressed between the ferrule 66 and the body 24 to create a pressure point seal reducing compression forces against the cap snap feature and improving the seal between the sealing ring 50 and the body 24.

An L-shaped, small diameter passageway 80 is provided through the ferrule 66 for attachment of a thin, L-shaped guide wire 82 thereto. One leg of the passageway 80 extends through the center of the second and third portions 56, 58 and the other leg of the passageway 80, which is perpendicular to the first leg, extends through the first portion 54. The corresponding legs of the L-shaped guide wire 82 are seated within the legs of the L-shaped passageway 80. The L-shaped guide wire 82 is thin, preferably approximately 0.014 to 0.018 inches in diameter, and has a diameter which is equal to the inner diameter of the L-shaped passageway 80 at the end surface 60 so as to provide a tight fit between the L-shaped guide wire 82 and the L-shaped passageway 80. The one leg of the guide wire 82 extends through the entire length of the diaphragm lumen 44 such that the leg extends outwardly from the opposite end of the stent holder/compression instrument 20.

The second end section 42 of the diaphragm 34 is formed from an elongated annular wall 84 which has an outer diameter that is greater than the central wall section 38. A connecting wall 86 tapers gradually from the annular wall 84 to the central wall section 38. The wall which forms the annular wall 84 is thickened relative to the wall that forms the central wall section 38 and has a portion 88 which is thickened even more than the remainder of the annular wall 84 proximate to the tapered connecting wall 86 for reasons more thoroughly described herein. The thickened wall portion 88 is thickened 0.02 inches more in this area relative to the remainder of the annular wall 84. An annular sealing ring 90 is provided at the opposite end of the annular wall 84 and extends generally perpendicular to the annular wall 84. The inner diameter of the portion of the diaphragm lumen 44 in the annular wall 84 is greater than the inner diameter of the lumen 44 in the central wall section 38 and the inner diameter of the lumen 44 gradually tapers in the connecting wall 86 from the enlarged inner diameter in the annular wall 84 to the smaller inner diameter in the central wall section 38. The tapered connecting wall 86 tapers down gradually to create a funnel for loading the balloon catheter A. The thickened wall portion 88 forms an inner diameter which is smaller than the inner diameter defined by the annular wall 84, however, the inner diameter defined by the thickened wall portion 88 does not impede the entry of the balloon catheter A therein.

An open or through plastic ferrule 92 is inserted into the annular wall 84 of the diaphragm 34 to clamp the sealing ring 90 against the body wall 26 to seal the opposite end of the pressure chamber 36, see FIG. 2. The open ferrule 92 is formed from a tubular wall 94 which has an annular ring 96 extending radially therefrom at one end thereof. A through bore 98 is provided through the open ferrule 92 which provides an access passageway for insertion of a stent 22 in a neutral state into the diaphragm lumen 44 as described herein. At the end of the tubular wall 94 opposite to the annular ring 96, a chamfer 99 is provided. The tubular wall 94 of the open ferrule 92 is inserted within the annular wall 84 such that the annular wall 84 is not compressed against the interior surface of the body wall 26, see FIG. 2. The annular ring 96 abuts against the sealing ring 90 to sandwich the sealing ring 90 between the annular ring 96 and the body wall 26.

A plastic end cap 100 snap-fits with the body wall 26 to maintain the open ferrule 92 in position and to maintain the clamp between the annular ring 96, the sealing ring 90 and the body wall 26. The end cap 100 includes an end wall 102 and an annular skirt 104 which depends therefrom. The annular end wall 102 has a through bore 106 therethrough that is aligned with the ferrule through bore 98 to provide an access passageway for the separate insertion of the stent 22 and the balloon catheter A as described herein and withdrawal of the stent-loaded balloon catheter. An internal, annular protrusion 108 projects inwardly from the annular skirt 104 and mates with an annular groove 110 that is provided in the external surface of the body wall 26 at a distance that is spaced from the end of the wall 26 to provide a snap-fit of the end cap 100 with the body 24. The annular end wall 106 of the end cap 100 abuts against the annular ring 96 of the ferrule 92 when the end cap 100 is snap-fit to the body 24 to maintain the ferrule 92 within the diaphragm lumen 44 and to maintain the seal between the ferrule 92, the sealing ring 90 and the body 24. The body wall 26 has a raised seal ring 112 at the point at which the diaphragm sealing ring 90 is compressed between the ferrule 92 and the body 24 to create a pressure point seal reducing compression forces against the cap snap feature and improving the seal between the sealing ring 90 and the body 24.

Before insertion into the stent holder/compression instrument 20, the diaphragm 34 is shorter in length than the length shown in the drawings. When the diaphragm 34 is inserted and held in position by the respective ferrules 52, 92 and respective end caps 66, 100, the diaphragm 34 is stretched to provide the thinned-down central wall section 28 that makes expansion of the diaphragm 34 during a negative pressure condition more uniform. It has been found that for G.E. L.I.M. silicone rubber having a durometer of 25-55 shore A, the diaphragm 34 is to be stretched by a minimum of 25% stretch, with 31%–38% being preferred, of its overall length. One of ordinary skill in the art would recognize that for different materials and for different durometers, the amount of stretch could vary. The wall of the central wall section 38 of the diaphragm 34 is preferably about 0.010 inches after stretched. When the diaphragm 34 is stretched, the diaphragm's inner diameter is reduced down to approximately the stent's proper compressed outer diameter. This eliminates wrinkles on the diaphragm 34 when the stent holder/compression instrument 20 is pressurized to crimp the stent 22 down onto the balloon catheter A, thus keeping surface contact between the diaphragm 34 and the stent 22 uniform and circumferentially continuous.

The first embodiment of the diaphragm 34 includes a holding structure 114 for lightly gripping the stent 22 when it is placed within the diaphragm lumen 44 even when the diaphragm 34 is subjected to a negative pressure condition as described herein to hold the stent 22 in its original placed position. The first embodiment of the diaphragm 34 also includes a positioning structure 116 for properly positioning the stent 22 within the diaphragm lumen 44 during original placement of the stent 22 therein.

The holding structure 114 is formed from a thickened wall portion 118 which is integrally formed with the diaphragm 34 along the length of the thin central wall section 38 and extends radially therefrom. The thickened wall portion 118 is continuous around the circumference of the central wall section 38. The thickened wall portions 118 contacts the inner wall which defines the body bore 28 when the diaphragm 34 is subjected to a negative pressure condition or when the diaphragm 34 is at rest and is not subjected to a negative pressure condition as described herein. The thickened wall portion 118 does not extend into the groove 30 and therefore, does not interfere with the transmission of fluid, such as air or a liquid, such as saline solution or other like liquids, (both of which are used as described herein), along the groove 30.

The positioning structure 116 is formed from a thickened wall portion 120 which causes a restriction 122 in the central section 38 of the diaphragm 34. The thickened wall portion 120 contacts the inner wall of the diaphragm 34 that defines the body bore 28 and the thickened wall portion 120 defines an inner diameter that is smaller than the outer diameter of the stent 22 in a neutral state that is to be placed and held in the diaphragm 34. The thickened wall portion 120 does not extend into the groove 30 and therefore, does not interfere with the transmission of fluid along the groove 30. The thickened wall portion 120 may extend circumferentially around the central wall section 38 or may be formed from a plurality of thickened wall portions arranged circumferentially around the central wall section 38 so long as an inner diameter which is less than the outer diameter of the stent 22 in the neutral state to be placed therein is formed by the positioning structure 116.

The fluid coupling 32 provided on the body 24 provides a through port 124 which communicates with the pressure chamber 36 between the diaphragm 34 and the body wall 26 for both pressurization and evacuation, that is subjecting the diaphragm 34 to a negative pressure condition, of the pressure chamber 36 by a coupled syringe instrument, shown only partially at 126. The syringe instrument 126 is coupled to the fluid coupling 32 and is employed for both pressurizing and depressurizing the operating fluid, i.e. air or liquid as described herein, within the stent holder/compression instrument 20, as more fully described hereinafter. A preferred syringe instrument 126 of the type which features a quick release mechanism which allows precise control of both initial and final fluid pressurization is described for example in U.S. Pat. No. 5,168,757. As shown in FIG. 2, the tubular portion 94 of the ferrule 92 extends axially beyond the port 124 of the fluid coupling 32 in order to support the diaphragm annular wall 84 and deter induced deflection of the annular wall 84 which could otherwise be drawn against the port 124 by suction action of the evacuation pressure reduced by the action of the syringe instrument 126.

As shown in FIG. 2, the stent 22 is not yet mounted within the stent holder/compression instrument 20 of the present invention. The initial inner diameter of the diaphragm lumen 44 in the central section 38 is slightly less than the desired final outer diameter of the stent 22, once compressed onto the balloon catheter A (this compressed condition of the stent 22 on the balloon catheter A is not shown in the drawings).

To load the stent 22 within the stent holder/compression instrument 20, initially with regard to the stent 22 per se as shown in FIG. 4, a tubular plastic mandrel 128 is inserted into a through bore of a tubular stent push sleeve 130 until the inserted end of the mandrel 128 contacts an inserted end of an eject rod 132 which has been inserted into the opposite end of the through bore in the tubular stent push sleeve 130. Next, as shown in FIG. 5, the mandrel 128 is passed through the stent 22 until the stent 22 stops against the end of the stent push sleeve 130 to form an assembly. The mandrel 128 has an outer diameter which is approximately equal to the inner diameter of the stent 22 in the neutral state.

Figure 6:
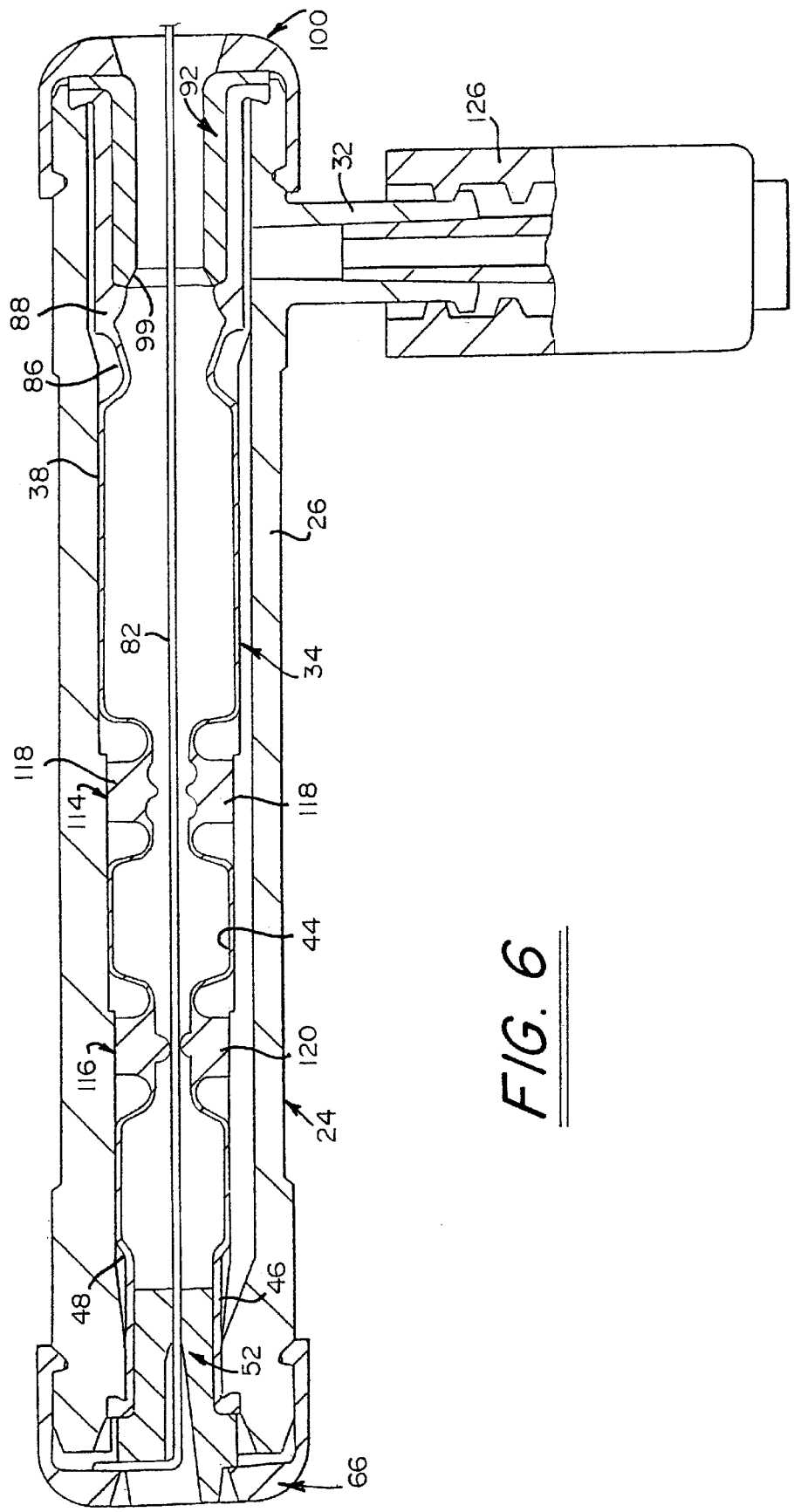
FIG. 6 is a cross-sectional view of the stent holder/compression instrument shown in FIG. 1, with a diaphragm therein being subjected to a negative pressure condition.

At this point, only air, not liquid, is provided in the pressure chamber 36. Thereafter, as shown in FIG. 6, the pressure chamber 36 is subjected to a negative pressure condition or partial vacuum which causes the portion of the flexible diaphragm 34 between the connecting wall 48 and the positioning structure 116, the portion of the flexible diaphragm 34 between the positioning structure 116 and the holding structure 114, and the portion of the flexible diaphragm 34 between the holding structure 114 and the connecting wall 86 to expand, thereby enlarging the inner diameter of the majority of the diaphragm lumen 44. During this enlargement, connecting walls 48, 86 roll towards the inner wall which defines the central bore 28 of the body 24. The inner diameter of the lumen 44 within the holding structure 114 and the positioning structure 116 does not expand because the thickened walls 118, 120 are not designed to expand when the portions on either side thereof are expanded. The pressure chamber 36 is subjected to a negative pressure condition by connecting the syringe instrument 126 thereto and pulling air out of the pressure chamber 36. Air flows along groove 30 to pass by the thickened wall portions 118, 120 which form the holding structure 114 and the positioning structure 116, respectively.

Next, the mandrel 128 is inserted onto the end of the guide wire 82 without handling the stent 22 (coated or uncoated), and is pushed axially through the diaphragm 34 by moving the push sleeve 130 and eject rod 132 so that the mandrel 128 passes through the central bore 98 of the ferrule 92 and into the diaphragm lumen 44 until the mandrel 128 contacts the end surface 60 of the ferrule 52 at the opposite end of the stent holder/compression instrument 20. The mandrel 128 may have an outer diameter which is smaller than the restricted lumen inner diameters formed by the holding structure 114 and the positioning structure 116. As the mandrel 128 is inserted, the stent 22 mounted thereon passes through the central bore of the ferrule and into the diaphragm lumen 44. The stent 22 cannot travel axially any further along the length of the diaphragm lumen 44 past the restriction 122 formed by the positioning structure 116 because the inner diameter defined by the restriction 122 in the positioning structure 116 is smaller than the outer diameter of the stent 22 in the neutral state. Thus, once the mandrel 128 contacts the end surface 60 of the ferrule 52, the stent 22 is encapsulated or mounted within the diaphragm 34.

Figure 8:
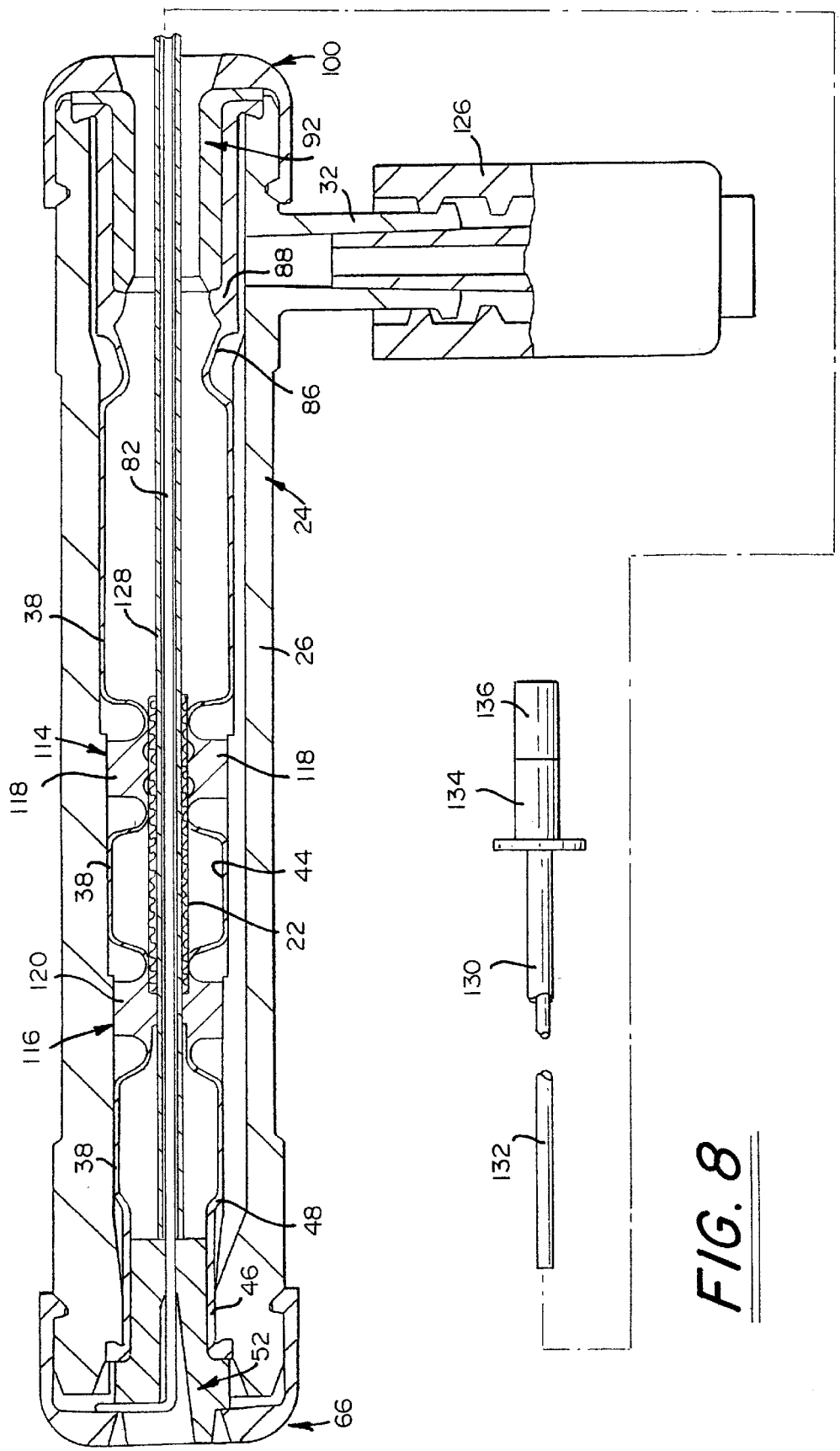
FIG. 8 is a cross-sectional view of the stent holder/compression instrument shown in FIG. 1, with the diaphragm therein being subjected to a negative pressure condition and with a portion of the assembly of FIG. 5 inserted therein and a portion of the assembly being removed.

Thereafter, as shown in FIG. 7, the push sleeve 130 is moved axially into the diaphragm lumen 44 until the stent 22 contacts the positioning structure 116, if the stent 22 had not previously been in contact with the positioning structure 116 by action of the initial insertion of the stent 22 on the mandrel 128. The stent 22 can slide along the mandrel 128 until it comes into contact with the positioning structure 116. Thereafter, the push sleeve 130 is pulled back until a handle 134 provided on the push sleeve 130 contacts a handle 136 provided on the eject rod 132 and the push sleeve 130 and the eject rod 132 are pulled out of the stent holder/compression instrument 20 leaving only the stent 22 and the mandrel 128 within the diaphragm 34 as shown in FIG. 8. Once properly positioned, the stent 22 is lightly gripped by the holding structure 114 when the pressure chamber 36 is subjected to a negative pressure condition, as shown in FIGS. 8 and 9.

Thereafter, the negative pressure within the pressure chamber 36 is relieved, thus effectively re-pressurizing the pressure chamber 36 to it's neutral or at rest configuration to cause the diaphragm 34 to conform to the stent 22 as shown in FIG. 10, but not effect compression of the stent 22. In this neutral or at rest configuration, the stent 22 is not tightly compressed by air pressure in the pressure chamber 36 and is lightly gripped by the holding structure 114 so as to maintain the stent's position within the diaphragm 34. The stent holder/compression instrument 20, with the stent 22 properly positioned therein, is now ready to be shipped such that the stent holder/compression instrument 20 acts as a shipping device. The mandrel 128 supports the stent 22 and deters deformation of the stent 22 during shipment. As can be seen from above, the stent 22 is not directly handled by an operator during loading of the stent 22 into the instrument 20, thus eliminating possible damage to the stent 22 or any coating thereon.

In use during an angioplasty procedure, the stent 22 is crimped onto the conventional balloon catheter A. Balloon catheters are known in the art and are formed from an angioplasty balloon B which is mounted on a catheter C. The catheter C has lumens (not shown), for inflating the angioplasty balloon B, and a central bore D through which the guide wire 82 is passed.

Before the balloon catheter A is inserted within the stent holder/compression instrument 20, the mandrel 128 is removed and the pressure chamber 36 is subjected to a negative pressure condition so as to cause the portions of the diaphragm 34 to expand as described herein. A deflated balloon catheter A is engaged onto the end of the guide wire 82 by the central bore D in the catheter C. The balloon catheter A is passed through the central bores 106, 98 of the end cap 100 and the ferrule 92, into the diaphragm lumen 44, and through the stent 22 until the tip of the catheter C contacts the end surface 60 of the ferrule 52 at the opposite end of the instrument 20 and the balloon B is positioned within the stent 22. The stent 20 is securely held in position by the holding structure 114 when the diaphragm 34 is expanded to allow the balloon catheter A to enter and pass and through the stent 22. The tapered connecting wall 86 creates a funnel for loading the balloon catheter A. This feature, in combination with the widened end surface 60 provided by the ferrule 52, allows for the easier placement of the balloon catheter A within the diaphragm 34 in the correct position.

Thereafter, the air in the pressure chamber 36 is purged from the stent 20 and liquid, preferably saline solution, is injected into the pressure chamber 26 to pressurize it and to cause the diaphragm 34 to uniformly compress the stent 22 around 360° and along the entire length of the stent 22 onto the deflated angioplasty balloon until the stent 22 is securely attached or crimped onto the deflated angioplasty balloon. The holding structure 114 compresses during pressurization to compress the stent 22 onto the deflated angioplasty balloon. The pressure chamber 36 is pressurized by injecting the saline solution into the pressure chamber 36 via the syringe instrument 126. Fluid flows along the groove 30 to pass by the thickened wall portions 118, 120 which form the holding structure 114 and the positioning structure 116, respectively. Use of the flexible diaphragm 34 to compress the stent 22 onto the balloon catheter A insures complete, uniform compression about a full 360° and along the entire length of the stent 22. As such, the stent 22 is affixed to the balloon catheter A in a manner which insures attachment during movement through a patient's vascular system, yet precludes damage to the balloon B. A more detailed discussion of this aspect of the invention and disclosure can be found in application Ser. No. 08/745,317 noted above, which disclosure has been incorporated by reference herein.

The instrument 20 is then subjected to a second negative pressure condition to partially evacuate the saline solution from the pressure chamber 26 and the balloon catheter A, which has the stent 22 crimped thereon, is removed from the instrument 20, and is ready for use by the surgeon. During removal of the balloon catheter A, which has the stent 22 crimped thereon, the chamfer 99 eliminates a sharp edge on the ferrule 92, thereby preventing the stent 22 from stripping off the angioplasty balloon B. The chamfer 99 also acts as a funnel for the balloon catheter A and stent 22 removal.

While it has been described that air is provided in the pressure chamber 26 during removal of the mandrel 128, the air could be purged and saline solution could be injected prior to expansion of the diaphragm 34 such that the stent holder compression instrument 20 would be operated with saline solution from this point onward. It has been found, however, that if liquid is used at this point, the stent 22 can lock up on the mandrel 128 making removal of the mandrel 128 from the stent 22 difficult.

The guide wire 82 provides several benefits in the present invention. First, the guide wire 82 facilitates loading of the balloon catheter A into the stent holder/compression instrument 20 and prevents entry of the balloon catheter A into the ferrule passageway 80. Second, the guide wire 82 fills the central bore D in the catheter C tip to prevent the diaphragm 34 from entering the catheter bore D under high crimping pressure conditions. This prevents extrusion of the diaphragm 34 down the catheter bore D and blowing out during crimping pressurization. It has been found that if a guide wire 82 is not used to fill the tip of the catheter bore D, the diaphragm 34 tends to extrude down the catheter bore D and blow out during crimping pressurization if the catheter C is not butted tightly against the end surface 60 of the ferrule 52. Crimping pressures sometimes cause a catheter C to slightly back out of the stent holder/compression instrument 20, and a blow out of the diaphragm 34 could occur even when care is exercised to place the tip of the catheter C against the end surface 60 of the ferrule 52 if the tip of the catheter C is not otherwise filled. Third, the guide wire 82 provides an operator more freedom in locating the stent 22 upon a balloon B. Catheter balloon locations vary by the manufacturer. When stents 22 are factory pre-loaded into the stent holder/compression instrument 20 as in the present invention, the surgeon's catheter choice cannot be predicted. Various dimensions from the catheter tip to the balloon center must be accommodated by the stent holder/compression instrument 20. With a guide wire 82 as used in the present invention, longitudinal centering of a stent 22 on a balloon can be accomplished without risk of diaphragm 34 blow-out if the catheter tip ends up short of the end surface 60 of the ferrule 52. Fourth, the guide wire 82 aids in providing centering to prevent a tip of a catheter C from snagging on the stent 22 during insertion. Finally, because balloon catheters A are commonly exchanged over guide wires during actual angioplasty procedures, the loading process is very familiar to catheter laboratory personnel and therefore, minimal training to load the balloon catheter A into the stent holder/compression instrument 20 is required.

Another feature of the present invention is that the annular wall portion 46 of the diaphragm 34 is thickened over a greater length allowing the tip of the catheter C to be encapsulated and protected when the tip of the catheter C is exposed to higher pressures during crimping pressurization. It has been found that when a thin diaphragm wall was used to surround the tip of the catheter, the diaphragm tended to extrude into the gap between the catheter tip and the end surface 60 of the ferrule 52 which caused blow outs of the diaphragm during crimping pressurization. The thicker annular wall 46 also helps insure if a guide wire 82 is not used, that the tip of the catheter does not "side step" and end up between the ferrule 52 and the diaphragm 34 as has been found to occur when a thin diaphragm wall was used to surround the tip of the catheter.

With regard to the provision of the thickened wall portion 88 provided in the present invention, it has been found that when a thinner wall portion was used proximate to the end of the ferrule 92, this thinner wall portion would tend to "roll" into the bore 98 of the ferrule 92 during crimping pressurization or under high pressure and burst. The thickened wall portion 88 in the diaphragm 34 prevents such a rolling action and blocks the gap between the catheter C and the diaphragm 34 during compression and tightens around the catheter C to prevent movement. Also, while a Touhey-Borst could be incorporated integrally in the end of the stent holder/compression instrument 20 to prevent such a rolling action of a thin-walled diaphragm, the novel thickened wall portion 88 provided in the present invention eliminates the need for a Touhey-Borst.

Figure 11:
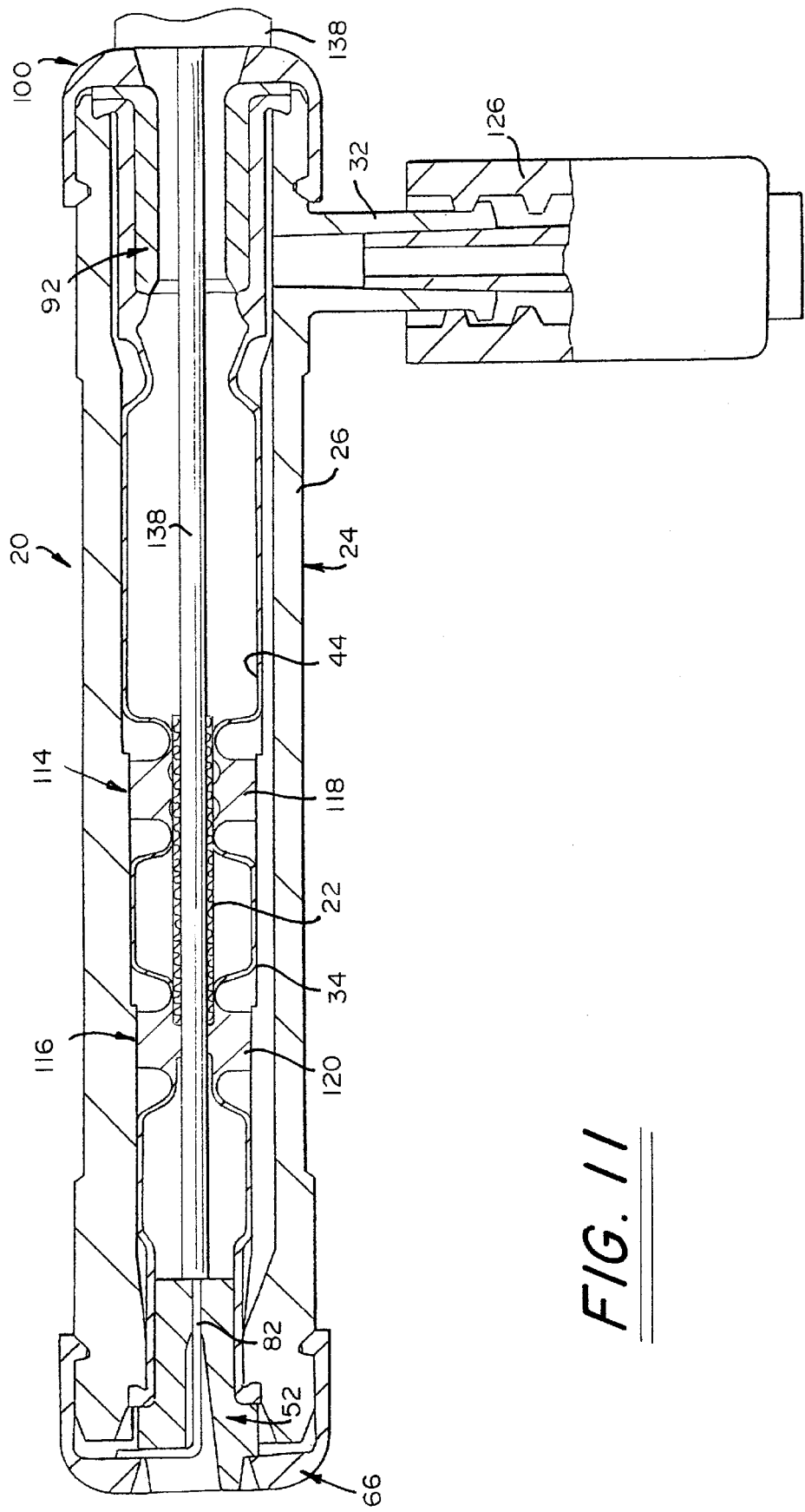
FIG. 11 is a cross-sectional view of the stent holder/compression instrument shown in FIG. 1, with the diaphragm therein being subjected to a negative pressure condition and having the stent positioned therein with a protective pin being positioned in the stent.

As shown in FIG. 11, the mandrel 128 has been eliminated and replaced by a protective pin 138 which has a portion that is approximately equal to the stent 22 and extends from the stent holder/compression instrument 20. The pin 138 aids in maintaining the stent 22 in its proper position; the pin 138 supports the stent 22; and deters deformation of the stent 22 during shipment.

Figure 14:
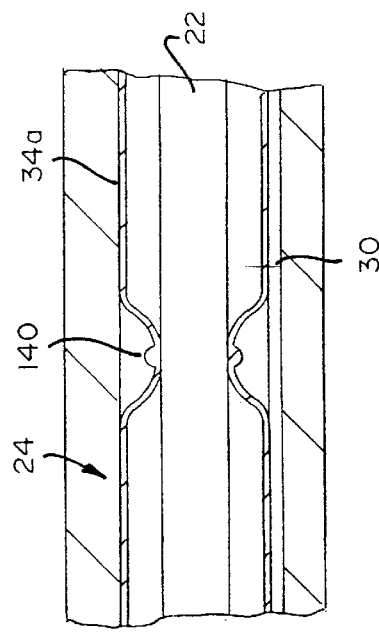
FIG. 14 is an enlarged cross-sectional view of the stent holder/compression instrument shown in FIG. 13, showing the diaphragm having the stent positioned therein and being subjected to a negative pressure condition.

Attention is now directed to FIGS. 13 and 14, which show an alternate embodiment of the diaphragm 34*a* used in the stent holder/compression instrument 20. The stent holder/compression instrument 20 shown in FIG. 13 and 14 is identical to that shown in FIGS. 1–12 and provides all of the same advantages and features as the stent holder/compression instrument 20 shown in FIGS. 1–12, except that the structure of the diaphragm 34*a* is different. Therefore, in the drawings, the other elements are numbered with identical reference numerals, with the exception that the suffix "a" is included after the numeral of the elements of the diaphragm 34*a*.

The diaphragm 34*a* is a flexible, generally tubular member mounted within the central bore 28 of the body 24 and the ends of the diaphragm 34*a* are sealed to the body 24 to form a pressure chamber 36 between the diaphragm 34 and the body 24. The diaphragm 34*a* has an elongated, thin wall section 38*a* along a central portion thereof which is generally tubular and which is integrally formed with first and second end sections 40*a*, 42*a*, respectively. A central lumen 44*a* extends axially along the length of the diaphragm 34*a*. Like diaphragm 34, diaphragm 34*a* is formed from an elastomer, preferably silicone and preferably G.E. L.I.M. silicone rubber, durometer 25-55 shore A, capable of withstanding a 450 psi or greater pressure externally applied for transmission to the stent 22 inserted within the diaphragm 34*a* during the stent compression operation.

The first end section 40*a* of the diaphragm 34*a* is formed from an elongated, generally annular wall 46*a* which has an inner diameter that is greater than the inner diameter of the central wall section 38*a*. The wall which forms the generally annular wall 46*a* is thickened relative to the wall that forms the central wall section 38*a*. An annular sealing ring 50*a* is provided at one end of the wall 46*a* and extends generally perpendicular to the wall 46*a* for capture between the ferrule 52 and the body 24.

The second end section 42*a* of the diaphragm 34*a* is formed from an elongated annular wall 84*a* which has an inner diameter that is greater than the inner diameter in the central wall section 38*a*. A connecting wall 86*a* tapers gradually from the annular wall 84*a* to the central wall section 38*a*. The wall which forms the annular wall 84*a* is thickened relative to the wall that forms the central wall section 38*a* and has a portion 88*a* which is thickened even more than the remainder of the annular wall 84*a* proximate to the tapered connecting wall 86*a* for reasons which have been described herein. An annular sealing ring 90*a* is provided at the opposite end of the annular wall 84*a* and extends generally perpendicular to the annular wall 84*a* for capture between the ferrule 92 and the body 24. The inner diameter of the portion of the diaphragm lumen 44*a* in the annular wall 84*a* is greater than the inner diameter of the lumen 44*a* in the central wall section 38*a* and the inner diameter of the lumen 44*a* gradually tapers in the connecting wall 86*a* from the enlarged inner diameter in the annular wall 84*a* to the smaller inner diameter in the central wall section 38*a*. The thickened wall portion 88*a* forms an inner diameter which is smaller than the inner diameter defined by the annular wall 84*a*, however, the inner diameter defined by the thickened wall portion 88*a* does not impede the entry of the balloon catheter A therein.

Like diaphragm 34, before insertion of the diaphragm 34*a* into the stent holder/compression instrument 20, the diaphragm 34*a* is shorter in length than the length shown in the drawings. When the diaphragm 34*a* is inserted and held in position by the respective ferrules 52, 92 and end caps 66, 100, the diaphragm 34*a* is stretched as described herein to provide the thinned-down central wall section 28*a* that makes expansion of the diaphragm 34*a* during a negative pressure condition more uniform. Again, it has been found that for G.E. L.I.M. silicone rubber having a durometer of 25-55 shore A, the diaphragm 34 is to be stretched by a minimum of 25% stretch, with 31%–38% being preferred, of its overall length. One of ordinary skill in the art would recognize that for different materials and for different durometers, the amount of stretch could vary. The wall of the central wall section 38*a* of the diaphragm 34*a* is preferably about 0.010 inches after stretched. When the diaphragm 34*a* is stretched, the diaphragms inner diameter is reduced down to approximately the stent's proper compressed outer diameter.

The diaphragm 34*a* includes a holding structure 114*a* for lightly gripping the stent 22 when it is placed within the diaphragm lumen 44*a* even when the diaphragm 34*a* is subjected to a negative pressure condition as described herein to hold the stent 22 in its original placed position as shown in FIG. 14. In the second embodiment, the positioning structure 116 of the first embodiment is eliminated. The holding structure 114*a* is formed from a ring 140 which is formed from a thickened portion of the diaphragm 34*a*. The ring 140 is integrally formed with the diaphragm 34*a* along the length of the thin central wall section 38*a*, extends radially therefrom and surrounds the central section 38*a*. The ring 140 does not contact the inner wall which defines the body bore 28 when the diaphragm 34*a* is in its neutral position, shown in FIG. 13, or subjected to a negative pressure condition, shown in FIG. 14.

When the diaphragm 34*a* is at rest as shown in FIG. 13, the ring 140 lightly grips the stent 22 therein and the stent 22 is ready for shipping within the stent holder/compression instrument 20. When the diaphragm 34*a* is subjected to a negative pressure condition, the ring 140 maintains its light grip on the stent 22 and does not flex away from the stent 22 as the portions of the diaphragm 34*a* proximate to the ring 140 expand. When the chamber 38 is pressurized to crimp the stent 22 onto a balloon catheter, the ring 140 will move inwardly to compress the stent 22 onto the balloon catheter.

Attention is now directed to FIGS. 15–18 which show yet another embodiment of the diaphragm 34*b* used in the stent holder/compression instrument 20. The stent holder/compression instrument 20 shown in FIGS. 15–18 is identical to that shown in FIGS. 1–12 and provides all of the same advantages and features as the stent holder/compression instrument 20 shown in FIGS. 1–12, except that the structure of the holding structure 114*b* of the diaphragm 34*b* is different. Therefore, in the drawings, the other elements are numbered with identical reference numerals, with the exception that the suffix "b" is included after the numeral of the elements of the diaphragm 34*b*. In the third embodiment, the positioning structure 116 of the first embodiment is eliminated.

A pair of the holding structures 114*b* are provided in the third embodiment for lightly gripping the stent 22 when it is placed within the diaphragm lumen 44 even when the diaphragm 34 is subjected to a negative pressure condition to hold the stent 22 in its original placed position. The function of the holding structure 114*b* in the third embodiment is identical to that of the first embodiment. In addition, the method of inserting the diaphragm 34*b* into the body 26 and the method of loading a stent 22 into the diaphragm 34*b* is identical to that of the first embodiment, except that the positioning structure shown in the first embodiment is not provided and instead the stent 22 is gripped by the pair of holding structures 114*b* during shipment.

Each holding structure 114*b* is formed from a plurality of thickened wall portions 142 which are integrally formed with the diaphragm 34*b* along the length of the thin central wall section 38*b* and extend radially therefrom. Preferably, three such thickened wall portions 142 are provided for each holding structure 114*b* and are aligned with each other around the circumference of the central section 38*b*. As shown in FIGS. 16 and 17, this forms a tri-lobular configuration around the central section 38*b* of the diaphragm 36*b*. Each of the thickened wall portions 142 contacts the inner wall which defines the body bore 28 when the diaphragm 34*b* is subjected to a negative pressure condition or when the diaphragm 34*b* is at rest and is not subjected to a negative pressure condition as described herein. The thickened wall portions 142 do not extend into the groove 30 and therefore, do not interfere with the transmission of fluid along the groove 30. In addition, as shown in FIG. 18, when the diaphragm 34*b* is inserted into tubular wall 26 of the body 24, the tri-lobular configuration forms spaces 144 which aids in the transmission of fluid along the length of the central through bore 28 when the pressure chamber 36 is subjected to a negative pressure condition. It is to be understood that the holding structure 142 which is axially distal from entry end of the stent compression instrument 20 can be modified so as to provide a positioning structure like that of the first embodiment.

A portion of the tool 146 which is used to form the diaphragm 34*b* is shown in FIG. 19. The tool 146 has grooves 148 along its length which are used to form triangular portions 150 of the diaphragm lumen 44*b* at the points of the thickened wall portions 142.

While preferred embodiments of the present invention is shown and described, it is envisioned that those skilled in the art may devise various modifications of the present invention without departing from the spirit and scope of the appended claims.

The invention claimed is:

1. A stent compression instrument for holding a stent therein during shipment and for use in crimping the stent onto a balloon catheter, said stent compression instrument comprising: a body having opposite ends and an inner wall defining a central bore; a flexible diaphragm having opposite ends and having a generally tubular, thin wall defining an axial lumen along its length for allowing placement of a stent therein, said diaphragm being positioned within said central bore of said body, thereby defining a chamber between said diaphragm and said body, said diaphragm being expandable under a negative pressure condition to expand within said body and compressible under pressure to crimp the stent onto a balloon catheter, said diaphragm having holding structure associated therewith for holding the stent within said diaphragm lumen.

2. A stent compression instrument as defined in claim 1, wherein said holding structure comprises at least one thickened wall portion along the length of said diaphragm tubular wall, said thickened wall portion contacting the stent.

3. A stent compression instrument as defined in claim 2, wherein said at least one thickened wall portion further contacts said inner wall of said body when the stent is positioned therein, and structure associated with said chamber along substantially the length thereof which is not blocked by said thickened wall portion such that fluid can flow along substantially the length of said chamber.

4. A stent compression instrument as defined in claim 2, wherein a plurality of thickened wall portions are provided and said plurality of thickened wall portions are generally aligned with each other around the circumference of said diaphragm tubular wall and define an inner diameter which is approximately equal to the outer diameter of the stent in a neutral state.

5. A stent compression instrument as defined in claim 1, further including positioning structure associated with said diaphragm for positioning the stent within said diaphragm lumen and preventing the further movement of the stent relative to the diaphragm lumen when the stent is placed therein.

6. A stent compression instrument as defined in claim 5, wherein said positioning structure comprises a thickened wall portion along the length of said diaphragm tubular wall at a position where an end of the stent is to be placed.

7. A stent compression instrument as defined in claim 6, wherein said thickened wall portion defines an inner diameter which is less than the outer diameter of the stent in a neutral state.

8. A stent compression instrument as defined in claim 1, wherein said holding structure comprises at least one thickened wall portion along the length of said diaphragm tubular wall, and further including positioning structure associated with said diaphragm for positioning the stent within said diaphragm lumen and preventing the further axial movement of the stent relative to the diaphragm lumen when the stent is placed therein, said positioning structure comprising a thickened wall portion along the length of said diaphragm tubular wall at a position spaced from said holding structure; and structure associated with said chamber which is not blocked by said thickened wall portion of said holding structure or said thickened wall portion of said positioning structure such that fluid can flow along substantially the length of said chamber.

9. A stent compression instrument as defined in claim 8, wherein a plurality of thickened wall portions are provided for said holding structure and said thickened wall portions of said holding structure are generally aligned with each other around the circumference of said diaphragm tubular wall and define an inner diameter which is approximately equal to the outer diameter of the stent in a neutral state, and said thickened wall portion of said positioning structure defines an inner diameter which is less than the outer diameter of the stent in a neutral state.

10. A stent compression instrument as defined in claim 1, further including a ferrule member having a portion which is positioned within said lumen of one of said ends of said diaphragm, said one end of said diaphragm being sandwiched between said ferrule member and said body to provide a seal at an end of said chamber between said body and said diaphragm.

11. A stent compression instrument as defined in claim 10, wherein said portion of said ferrule member provides an end surface for contacting a balloon catheter inserted within said diaphragm lumen and prevents further axial movement of the balloon catheter relative to the diaphragm.

12. A stent compression instrument as defined in claim 10, further including a cap for securing said ferrule member to said body.

13. A stent compression instrument as defined in claim 12, wherein said cap and said body have structure for snap-fitting said cap to said body.

14. A stent compression instrument as defined in claim 1, further including a ferrule member having a through bore and a portion which is positioned within said lumen of one of said ends of said diaphragm, said one end of said diaphragm being sandwiched between said ferrule member and said body to provide a seal at an end of said chamber between said body and said diaphragm; and said diaphragm having a thickened wall portion adjacent to an end of said ferrule member, such that when said diaphragm expands under a negative pressure condition, said thickened wall portion does not enter into said through bore in said ferrule member.

15. A stent compression instrument as defined in claim 14, further including a cap for securing said ferrule member to said body.

16. A stent compression instrument as defined in claim 15, wherein said cap and said body have structure for snap-fitting said cap to said body.

17. A stent compression instrument as defined in claim 1, further including a guide wire associated with said lumen of said diaphragm and attached to said body for guiding the placement of a balloon catheter within said central bore of said diaphragm.

18. A stent compression instrument as defined in claim 1, further including second holding structure associated with said diaphragm for maintaining the position of the stent within the diaphragm once positioned therein.

19. A stent compression instrument as defined in claim 18, wherein said second holding structure comprises a pin which is inserted into said diaphragm lumen and through the stent.

20. The combination of a stent and a stent compression instrument as defined in claim 1.

21. A stent compression instrument as defined in claim 1, wherein said diaphragm is stretched when said diaphragm is positioned within said body to form said thin wall.

22. A stent compression instrument as defined in claim 21, wherein said diaphragm is stretched by a minimum of 25% when said diaphragm is positioned within said body to form said thin wall.

23. A stent compression instrument as defined in claim 1, wherein said holding structure holds said diaphragm within said diaphragm lumen when said diaphragm is expanded under a negative pressure condition to prevent movement of the stent once positioned within said diaphragm.

24. A stent compression instrument for use in crimping a stent onto a balloon catheter comprising: a body having opposite ends and an inner wall defining a central bore; a flexible diaphragm having opposite ends and having a generally tubular, thin wall defining an axial lumen along its length for allowing placement of a stent therein, said diaphragm being positioned within said central bore of said body, thereby defining a chamber between said diaphragm and said body, said diaphragm being expandable under a negative pressure condition to expand within said body and compressible under pressure to crimp the stent onto a balloon catheter; first sealing structure for providing a seal at an end of said chamber between said body and said diaphragm; second sealing structure for providing a seal at an end of said chamber between said body and said diaphragm; and said diaphragm having a thickened wall portion proximate to said second sealing structure for resisting deformation of said diaphragm when said diaphragm is subjected to a negative pressure condition.

25. A stent compression instrument as defined in claim 24, wherein said second sealing structure comprises a ferrule member having a through bore and a portion which is positioned within said lumen of one of said ends of said diaphragm, said one end of said diaphragm being sandwiched between said ferrule member and said body to provide said seal at said end of said chamber between said body and said diaphragm; said thickened wall portion being adjacent to an end of said ferrule member such that when said diaphragm expands under a negative pressure condition, said thickened wall portion does not enter into said through bore in said ferrule member.

26. A stent compression instrument as defined in claim 25, wherein said ferrule member has a chamfer at the end proximate to said thickened wall portion.

27. A stent compression instrument as defined in claim 26, further including a cap for securing said ferrule member to said body.

28. A stent compression instrument as defined in claim 27, wherein said cap and said body have structure for snap-fitting said cap to said body.

29. A stent compression instrument as defined in claim 24, wherein said first sealing structure comprises a ferrule member having an end portion which is positioned within said lumen of one of said ends of said diaphragm, said one end of said diaphragm being sandwiched between said ferrule member and said body to provide said seal at said end of said chamber between said body and said diaphragm.

30. A stent compression instrument as defined in claim 29, wherein said diaphragm has a thickened wall portion which surrounds said ferrule member and extends from said end portion of said ferrule member for surrounding a tip of a balloon catheter inserted within said diaphragm lumen.

31. A stent compression instrument as defined in claim 29, wherein said end portion of said ferrule member provides an end surface for contacting a balloon catheter inserted within said diaphragm lumen and prevents further axial movement of the balloon catheter relative to the diaphragm.

32. A stent compression instrument as defined in claim 29, further including a cap for securing said ferrule member to said body.

33. A stent compression instrument as defined in claim 32, wherein said cap and said body have structure for snap-fitting said cap to said body.

34. A stent compression instrument as defined in claim 24, further including a guide wire associated with said lumen of said diaphragm and attached to said body for guiding the placement of a balloon catheter within said central bore of said diaphragm.

35. A stent compression instrument as defined in claim 24, wherein said diaphragm further includes holding structure associated therewith for holding the stent within said diaphragm lumen.

36. A stent compression instrument as defined in claim 35, wherein said holding structure comprises at least one thickened wall portion along the length of said diaphragm tubular wall and spaced from said first-defined thickened wall portion.

37. A stent compression instrument as defined in claim 24, further including positioning structure associated with said diaphragm for positioning the stent within said diaphragm lumen and preventing the further movement of the stent into the diaphragm lumen when the stent is placed therein.

38. A stent compression instrument as defined in claim 37, wherein said positioning structure comprises a thickened wall portion along the length of said diaphragm tubular wall at a position where an end of the stent is to be placed and spaced from said first-defined thickened wall portion, said second-defined thickened wall portion defining an inner diameter which is less than the outer diameter of the stent in a neutral state.

39. A stent compression instrument as defined in claim 24, wherein said diaphragm is stretched when said diaphragm is positioned within said body to form said thin wall.

40. A stent compression instrument as defined in claim 39, wherein said diaphragm is stretched by a minimum of 25% when said diaphragm is positioned within said body to form said thin wall.

41. A stent compression instrument for use in crimping a stent onto a balloon catheter comprising: a body having opposite ends and an inner wall defining a central bore; a flexible diaphragm having opposite ends and having a generally tubular, thin wall defining an axial lumen along its length for allowing placement of a stent therein, said diaphragm being positioned within said central bore of said body, thereby defining a chamber between said diaphragm and said body, said diaphragm being expandable under a negative pressure condition to expand within said body and compressible under pressure to crimp the stent onto a balloon catheter; a guide wire associated with said lumen of said diaphragm and attached to said body for guiding the placement of a balloon catheter within said central bore of said diaphragm.

42. A stent compression instrument as defined in claim 41, further including sealing structure for providing a seal between said body and said diaphragm and said diaphragm further having a thickened wall portion proximate to said sealing structure.

43. A stent compression instrument as defined in claim 41, wherein said diaphragm further includes holding structure associated therewith for holding said stent within said diaphragm.

44. A stent compression instrument as defined in claim 41, further including positioning structure associated with said diaphragm for positioning the stent within said diaphragm lumen and preventing the further movement of the stent into the diaphragm lumen when the stent is placed therein.

45. A stent compression instrument for use in crimping a stent onto a balloon catheter comprising: a body having opposite ends and an inner wall defining a central bore; a flexible diaphragm having opposite ends and having a generally tubular, thin wall defining an axial lumen along its length for allowing placement of a stent therein, said diaphragm being positioned within said central bore of said body, thereby defining a chamber between said diaphragm and said body, said diaphragm being expandable under a negative pressure condition to expand within said body and compressible under pressure to crimp the stent onto a balloon catheter, said diaphragm being stretched when said diaphragm is positioned within said body to form said thin wall.

46. A stent compression instrument as defined in claim 45, said diaphragm being stretched by a minimum of 25% when said diaphragm is positioned within said body to form said thin wall.

47. A stent compression instrument as defined in claim 45, wherein said diaphragm further includes holding structure associated therewith for holding the stent within said diaphragm lumen.

48. A stent compression instrument as defined in claim 45, further including positioning structure associated with said diaphragm for positioning the stent within said diaphragm lumen and preventing the further movement of the stent into the diaphragm lumen when the stent is placed therein.

49. A method of inserting a stent into a stent compression instrument comprising the steps of: providing a stent compression instrument having a flexible diaphragm mounted within a body thereby defining a chamber between said diaphragm and said body, said chamber being sealed at opposite ends thereof, said diaphragm having opposite ends and defining an axial lumen therethrough, said lumen being sealed at one of said ends and open at the other of said ends, and holding structure associated with said diaphragm for holding a stent in position once said stent is mounted within said diaphragm even when said diaphragm is subjected to a negative pressure condition; creating a negative pressure condition around said diaphragm so as to expand said diaphragm; and placing said stent within said diaphragm lumen such that said holding structure holds said stent within said lumen during said created negative pressure condition.

50. A method as defined in claim 49, further including the steps of: providing a mandrel having opposite ends; providing an eject rod having opposite ends; providing a push sleeve having opposite ends an a central bore therethrough; inserting said mandrel into said push sleeve central bore through one of said push sleeve ends and inserting said eject rod into said push sleeve central bore through the other one of said push sleeve ends until said mandrel and said eject rod contact each other; mounting said stent on said mandrel; inserting said mandrel and said stent mounted thereon into said diaphragm lumen; and removing said push sleeve and said eject rod, thereby leaving said mandrel and said stent within said diaphragm lumen.

51. A method as defined in claim 50, further including the step of removing said mandrel, thereby leaving only said stent within said diaphragm.

52. A method as defined in claim 50, wherein said stent compression instrument includes sealing structure for sealing said end of said diaphragm, and wherein said mandrel is inserted into said lumen of said diaphragm until said mandrel contacts said sealing structure, said sealing structure preventing the further axial movement of said mandrel within said diaphragm lumen.

53. A method as defined in claim 49, further including the step of relieving said negative pressure condition to allow said diaphragm to return to a neutral condition.

54. A method as defined in claim 49, wherein said one end of said chamber is sealed by a ferrule member having an axial bore therethrough which sandwiches said diaphragm between said ferrule member and said body, such that said ferrule member opens said open end of said diaphragm.

55. A method as defined in claim 54, wherein said ferrule member having a chamfer at an end thereof.

56. A method as defined in claim 54, wherein said diaphragm further includes a thickened wall portion proximate to said ferrule member such that when said diaphragm is subject to said negative pressure condition, said thickened portion of said diaphragm does not enter said axial bore of said ferrule member.

57. A method of shipping a stent comprising the steps of: providing a stent compression instrument having a flexible diaphragm mounted within a body and positioning said stent within said flexible diaphragm, said flexible diaphragm holding said stent therein during shipping.

58. A method as defined in claim 57, wherein said diaphragm has positioning structure for maintaining the stent's position within said diaphragm during shipment.

* * * * *